(12) United States Patent
Bureau et al.

(10) Patent No.: US 11,998,181 B2
(45) Date of Patent: Jun. 4, 2024

(54) LAPAROSCOPIC MORCELLATION BAG AND LAPAROSCOPIC MORCELLATION KIT INCLUDING A MORCELLATION BAG

(71) Applicant: DEFLASTRAT, S.L.U., San Sebastián (ES)

(72) Inventors: Maxime Pierrick François Bureau, San Sebastián (ES); Iñigo Abreu de Con, San Sebastián (ES); Carolina Vera Martin, San Sebastián (ES)

(73) Assignee: DEFLASTRAT, S.L.U., San Sebastián (ES)

( * ) Notice: Subject to any disclaimer, the term of this patent is extended or adjusted under 35 U.S.C. 154(b) by 601 days.

(21) Appl. No.: 17/415,767

(22) PCT Filed: Dec. 17, 2019

(86) PCT No.: PCT/ES2019/070853
§ 371 (c)(1),
(2) Date: Jun. 18, 2021

(87) PCT Pub. No.: WO2020/128127
PCT Pub. Date: Jun. 25, 2020

(65) Prior Publication Data
US 2022/0061830 A1    Mar. 3, 2022

(30) Foreign Application Priority Data

Dec. 19, 2018 (ES) .............. ES201831245

(51) Int. Cl.
*A61B 17/00* (2006.01)
*A61J 1/10* (2006.01)
(Continued)

(52) U.S. Cl.
CPC .......... *A61B 17/00234* (2013.01); *A61J 1/10* (2013.01); *A61J 1/1468* (2015.05);
(Continued)

(58) Field of Classification Search
CPC ....... A61J 1/10; A61J 1/1468; A61B 17/3474; A61B 2017/00287; A61B 2017/00292; A61B 2017/00867; A61B 2017/00907
See application file for complete search history.

(56) References Cited

U.S. PATENT DOCUMENTS 6,270,505 B1    8/2001  Yoshida et al.
6,797,398 B2    9/2004  Suzuki et al.
(Continued)

FOREIGN PATENT DOCUMENTS

EP    1304218 A1    4/2003
KR    101739225 B1    5/2017
(Continued)

*Primary Examiner* — Thomas McEvoy
(74) *Attorney, Agent, or Firm* — The Webb Law Firm (57) ABSTRACT

The disclosure relates to a morcellation bag including at least one film of plastic material attached so as to define a surface of the bag with a first closed end and a second open end for introducing surgical specimens and a morcellator; characterized in that it is provided with at least one transparent region, said transparent region having an area of at least 1 cm² and a thickness less than 200 μm; said transparent region being made of a material or materials with a total transmittance greater than 80%, a clarity greater than 80% and a haze less than 25%.

12 Claims, 6 Drawing Sheets

(51) Int. Cl.
 *A61J 1/14* (2023.01)
 *A61B 17/34* (2006.01)
(52) U.S. Cl.
 CPC ............ *A61B 2017/00287* (2013.01); *A61B 2017/00292* (2013.01); *A61B 2017/00867* (2013.01); *A61B 2017/00907* (2013.01); *A61B 17/3474* (2013.01)

(56) References Cited

U.S. PATENT DOCUMENTS

| | | |
|---|---|---|
| 6,958,069 B2 | 10/2005 | Shipp et al. |
| 2006/0200170 A1 | 9/2006 | Aranyi |
| 2013/0184536 A1 | 7/2013 | Shibley et al. |
| 2013/0325025 A1 | 12/2013 | Hathaway et al. |
| 2014/0236167 A1 | 8/2014 | Shibley et al. |
| 2014/0236168 A1 | 8/2014 | Shibley et al. |
| 2017/0231611 A1 | 8/2017 | Holsten et al. |

FOREIGN PATENT DOCUMENTS

| | | |
|---|---|---|
| WO | 02056754 A2 | 7/2002 |
| WO | 2016028429 A1 | 2/2016 |

LAPAROSCOPIC MORCELLATION BAG AND LAPAROSCOPIC MORCELLATION KIT INCLUDING A MORCELLATION BAG

CROSS-REFERENCE TO RELATED APPLICATIONS

This application is the U.S. national phase of International Application No. PCT/ES2019/070853 filed Dec. 17, 2019, and claims priority to Spanish Patent Application No. P201831245 filed Dec. 19, 2018, the disclosures of which are hereby incorporated by reference in their entirety.

BACKGROUND OF THE DISCLOSURE

Field of the Disclosure

The present disclosure is comprised within the technical sector of medical instruments and devices.

More particularly, the present disclosure relates to a laparoscopic morcellation bag, as well as to a laparoscopic morcellation kit including a morcellation bag, for use, as a non-limiting example, in hysterectomy and myomectomy interventions.

Description of Related Art

Laparoscopy is a surgical technique which involves introducing medical instruments into the pelvic and/or abdominal cavity of the patient through at least one small incision, usually between 0.5 and 1.5 cm in length.

It is a minimally invasive surgery, therefore it is frequently used, among other applications, in women with gynecological pathologies. As a non-limiting example, it is used in hysterectomy interventions (complete or partial removal of the uterus) and myomectomy (removal of myomas).

Compared with laparotomy, a surgical intervention which involves the opening of the abdominal walls and leaving the underlying organs exposed, surgeries based on laparoscopy have, among others, the following advantages: shorter hospital stay, shorter recovery time and reduction of the time of recuperation and lower morbidity.

To enable using surgical procedures based on laparoscopy it is sometimes necessary to resort to electromechanical morcellation (EEM). Said morcellation procedures roughly consist of breaking up at least one surgical specimen (i.e., at least one portion of tissue from the patient) into smaller pieces with a surgical instrument called a morcellator so that they can be extracted from the body of the patient through a small incision that is made for a trocar, without having to make additional incisions or make the incision or incisions previously made for introducing medical instruments larger for that purpose.

In 2014, the US Food and Drug Administration (FDA) issued a declaration discouraged the use of EEM for hysterectomy and myomectomy in women with uterine fibromas suspected of developing into a tumor given the risk of the involuntary spreading of a malignancy. The FDA estimated the risk of occult sarcoma to be 1 in 350 women.

As a result, the need to develop devices that allowed the use of laparoscopic techniques in surgical procedures such as hysterectomy and myomectomy emerged in the sector, which at the same time eliminate or significantly lower the risk of the involuntary spread of malignant cells coming from the surgical specimen or specimens. This process culminated in the emergence of so-called "morcellation bags".

Morcellation bags are introduced into the pelvic-intestinal cavity of the patient in order to perform morcellation operations therein. It is thereby possible to confine the morcellation to a closed space that is isolated from the tissues of the patient, so as to prevent the involuntary spread of malignant cells. Today, about 600,000 hysterectomies are performed in the United States, 30% of which are performed by laparoscopic surgery, and the procedure for all these operations is currently evolving so that they can be performed with morcellation bags.

Nevertheless, morcellation bags available today have a number of drawbacks.

Thus, for example, U.S. Pat. No. 9,044,210 discloses morcellation bags which are necessarily provided with two different open ports (or port holes):
  a main open port, through which the surgical specimen or specimens and the morcellator (apparatus used to perform morcellation) are introduced; and
  an open side port, through which the optical devices and insufflation devices are introduced.

Optical devices allow the medical team to maintain a view of the inside of the bag to carry out morcellation. In this sense, it is particularly important for the medical team to be able to determine, without error, the separation between the morcellator blade and the bag to assure the integrity of said bag and prevent iatrogenesis (damage caused by medical acts).

Insufflation devices are used to inflate the morcellation bag by introducing a gas into same, for example carbon dioxide, to augment its size and leave enough space inside the bag for the medical team to perform morcellation.

The morcellation bags according to U.S. Pat. No. 9,044,210 are hard to use because the incisions made in the skin of the patient for such use coincide with the ports of the bag. Furthermore, the method for placing them is long and requires carrying out a number of different steps (more than 15), which translates into the intervention time also being long and there being many possibilities of making a mistake.

Likewise, said morcellation bags no are completely hermetic because the open side port, which can become contaminated if it comes into contact with the surgical specimen or specimens or pieces thereof (which detach during morcellation), has to pass through the abdomen of the patient again during the process extracting the morcellation bag. This lowers the risk of contamination of the abdomen with respect to morcellation procedures performed without a bag, but it does not entirely eliminate said risk.

Moreover, patent application no. US 20160183932 discloses morcellation bags provided with a single open port. These bags have the following drawbacks:
  A laparotomy must be performed in the abdomen in order to use them, so in most cases, the incision that has to be made is large enough so as to extract the surgical specimen or specimens without the need for morcellation; and
  Optical devices and the morcellator have to be introduced through the same incision in the abdomen. This reduces the side view of the end of the morcellator by more than 70% and generates many blind spots.

Patent application nos. US 20140236167, US 20140236168 and US 20130184536 disclose morcellation bags provided with a single open port, through which the surgical specimen or specimens, the morcellator and insufflation devices are introduced. In these morcellation bags, the optical devices are introduced by perforating the wall of the bag using a second additional trocar.

The impenetrability of the bag is annulled when it is perforated in the abdomen of the patient. Furthermore, when the second trocar perforates the morcellation bag, it comes into contact with the inside of said bag, which may be contaminated by the surgical specimen or specimens, or pieces thereof. During the extraction of said second trocar, the sheath of said device necessarily passes through the abdominal wall, possibly contaminating it.

Likewise, optical devices also come into contact with the inside of the morcellation bag without being provided with protection, so they suffer the risk of being contaminated. This makes it extremely difficult for said optical devices to be reused.

In fact, this latter solution proposed in the state of the art, which consists of introducing optical devices by perforating the wall of the morcellation bag, has been rejected by the FDA health authorities because of the risk of contamination it entails.

Other Examples of laparoscopic morcellation bags are given in the following prior art documents: U.S. Pat. No. 6,270,505, US2013325025, US2006200170, WO2016028429 and WO02056754.

SUMMARY OF THE DISCLOSURE

Throughout the present disclosure, the "total transmittance" of a material must be understood to mean the amount of light expressed as a percentage which is transmitted through said material with respect to the total amount of incident light, measured according to international standard ASTM D 1003, using to that end a transmission beam measurement device (a hazemeter).

Total transmittance has two components:
direct transmittance: i.e., the proportion of light that is transmitted through the material without changing its direction; and
diffuse transmittance: i.e., the proportion of light that is scattered upon transmission (i.e., its direction changes). This scattering may be due to both reflections of the light on the surface of the material and to reflections within said material.

Likewise, the "clarity" of a material must be understood to mean the proportion of light transmitted through said material which is scattered at an angle of less than 2.5°, measured according to international standard ASTM D 1003, using to that end a transmission beam measurement device (a hazemeter).

Finally, the "haze" of a material must be understood to mean the proportion of light transmitted through said material which is scattered at an angle of more than 2.5°, measured according to international standard ASTM D 1003, using to that end a transmission beam measurement device (a hazemeter).

For the purpose of solving the problems described in relation to the prior art, a first object of the present disclosure relates to a laparoscopic morcellation bag comprising:
at least one film of plastic material, attached such that it defines a surface of the bag;
said surface of the bag having a first closed end and a second open end, the second open end being a port for introducing at least one surgical specimen and a morcellator,
said laparoscopic morcellation bag being characterized in that it is provided with at least one transparent region, said transparent region having an area of at least 1 cm$^2$ and a thickness less than 200 µm, and said transparent region being made of a material or a combination of materials with a total transmittance greater than 80%, a clarity greater than 80% and a haze less than 25%.

The open end of the morcellation bags according to the present disclosure function as a port for introducing into the bag one or more surgical specimens of the patient and isolating them to thereby prevent them from coming into contact with the inner surface of the abdomen of the patient. A trocar, i.e., a medical device provided with a conduit, facilitating access of the surgical instrument to the inside of the bag, is subsequently fixed to said open end. Said trocar is provided with leak-tightness valves (a sealing valve and a check valve) as well as with a connection to the insufflation device. Through the conduit of the trocar is introduced a morcellator, a surgical device intended for morcellating (breaking up into pieces) the surgical specimens.

Moreover, the transparent region provided in the morcellation bags according to the present disclosure allows the optical devices to maintain a view of the inside of the bag upon coming into direct contact with said transparent region, without the surface needing to be perforated for said purpose. The need to provide the bag with a second open port intended for introducing optical devices is also thereby prevented, as is having to introduce the optical devices through the same open port through which the morcellation specimens and the morcellator are introduced, thus preventing contamination of the optical devices. Finally, the morcellation bags according to the present disclosure allow medical personnel to have a continuous view of the inside of the abdominal cavity, even during the extraction of the bag once the morcellation has ended, without any blind maneuvers since the optical device is always outside the bag. All this translates into a reduction in wait and intervention times and into a lower risk of error with respect to morcellation bags of the state of the art.

In a preferred embodiment of the present disclosure, the transparent region is made of a material or a combination of materials with a total transmittance greater than 90%, a clarity greater than 90% and a haze less than 4%.

The transparent region provided in the morcellation bag according to the disclosure preferably has a thickness of 80 µm. Likewise, the transparent region can preferably be made of polyurethane, polyester, polypropylene, polyethylene, polycarbonate, silicone and/or combinations thereof.

In another preferred embodiment of the morcellation bag according to the present disclosure, the second open end of the surface of the bag is provided with a drawstring. Said drawstring is intended for remaining outside the abdomen of the patient during the surgical intervention to facilitate subsequent extraction of the morcellation bag.

In a further preferred embodiment of the morcellation bag according to the present disclosure, the second open end of the surface of the bag is provided with a flexible ring with a Shore A hardness ≤90, which confers shape memory to same. This configuration allows opening the second end in a simpler manner, once the morcellation bag has been introduced into the abdomen of the patient and therefore facilitates the introduction of the surgical specimen or specimens into said bag.

In a more preferred embodiment of the disclosure, the flexible ring is of a color that allows being readily distinguished from the organs of the patient. The fact that the flexible ring is of a color allows it to be readily recognized in the abdomen of the patient, therefore preventing being able to confuse said ring with an organ of the patient. A preferred option is for the flexible ring to be black.

In another embodiment of the present disclosure, the flexible ring is attached to a drawstring.

In another embodiment of the present disclosure, the flexible ring is replaced with the drawstring bent into a loop shape, said loop being part of a taut-line hitch knot type attachment.

This loop, with the taut-line hitch knot type attachment, allows automatically closing the entrance of the bag by pulling on the drawstring, preventing the surgical specimen from getting out of the bag. The entrance of the bag is opened manually again once it is outside the abdomen so as to allow inserting the trocar.

In another embodiment of the laparoscopic morcellation bag according to the disclosure, the transparent region occupies an area greater than 60% of the total area of the surface of the bag, preferably an area greater than 80% of the total area of the surface of the bag, and more preferably, an area equal to the total area of the surface of the bag. In this latter case, the entire surface of the bag is made of a transparent material. Being made entirely of a transparent material allows placing optical devices at any point thereof in order to see the inside.

In a further embodiment of the disclosure, the surface of the bag is folded into an accordion shape. This specific type of folding makes it possible for the morcellation bag to automatically expand once it has been introduced into the abdominal cavity of the patient.

According to the present disclosure, the surface of the bag preferably has a round shape. The presence of folds and peaks which may disrupt the view when optical devices are supported against the transparent region of the inflated morcellation bag is thereby prevented.

In another embodiment of the present disclosure, the surface of the bag is folded telescopically. By means of this type of folding, the morcellation bag will expand automatically once it has been introduced into the abdominal cavity of the patient, and it furthermore facilitates complete sterilization of the bag, i.e. to the bottom of the bag, in the event of sterilization with the ethylene oxide gas.

In a preferred embodiment of the disclosure, the morcellation bag is provided with at least one hollow comprising an open outer mouth, a side surface hermetically attached to the surface of the bag and a closed bottom hermetically attached in turn to said side surface, the closed bottom furthermore being provided with a transparent region of an area of at least 1 cm² and a thickness less than 200 μm, and said transparent region being made of a material or a combination of materials with a total transmittance greater than 80%, a clarity greater than 80% and a haze less than 25%.

In this embodiment of the disclosure described in the preceding paragraph, the hollow has a tube shape and is intended for housing optical devices therein. Said hollow has a closed bottom provided with a transparent surface which allows the optical devices to see the inside of the bag, without any opening or hole needing to be made for that purpose in the surface of the bag. Likewise, the hollow is completely hermetic so as to prevent any possible contamination of the optical devices.

The hollows previously described furthermore improve the view of the inside of the bag in those cases in which the inner wall of the morcellation bag becomes dirty and aid in fixing the optical devices, limiting their movement.

The side surface of the hollow generally has a tubular shape. Nevertheless, the present disclosure also contemplates the possibility of said side surface being trapezoidal. This trapezoidal embodiment facilitates the introduction of the optical devices and limits their movement once they have been introduced into the hollow. Furthermore, the fact that the mouth of the hollow is narrower than the bottom of the hollow means that when the morcellation bag is inflated, the resulting pressure tightens the hollow around the optical devices at the mouth of said hollow, which contributes to a better hold of said optical devices and additionally limits their movement.

In a preferred embodiment of the disclosure, the hollow is provided with at least one projecting tab. Said tab or tabs facilitate the introduction of the optical devices into the hollow once the morcellation bag has been introduced into the abdominal cavity of the patient.

In another preferred embodiment of the disclosure, the width of the second open end of the bag is between 17 and 20 cm. It is considered that said width is sufficient so as to allow introducing into the morcellation bag most of the surgical specimens obtained in interventions of this type. In fact, it is estimated that the largest surgical specimen to be introduced into the morcellation bag would be a uterus, with a weight of about 1 Kg and 15 cm in diameter.

Likewise, in a final preferred embodiment of the disclosure, the surface of the bag has a Shore elastic stiffness greater than A70, an elongation at break greater than 100%, a mechanical breaking strength greater than 40 MPa and a continuous use temperature greater than 115° C.

A second object of the present disclosure relates to a laparoscopic morcellation kit comprising:
- a laparoscopic morcellation bag according to the first aspect of the disclosure; and
- an introducer tube containing the laparoscopic morcellation bag folded up therein.

In a preferred embodiment of the present disclosure, the laparoscopic morcellation kit comprises a trocar between 15 and 20 mm in diameter and between 70 and 100 mm in length, said trocar furthermore being provided with an inlet for the connection to insufflation devices.

Throughout the description reference will only be made to the morcellation bag being provided with a single transparent region for the sake of simplicity. Nevertheless, it should be mentioned that the present disclosure also expressly contemplates the possibility of the morcellation bag being provided with two or more different transparent regions or of the entire bag being transparent.

Likewise, throughout the description reference will only be made to a single hollow (in those embodiments of the disclosure which are provided with this element) for the sake of simplicity. Nevertheless, it should be mentioned that the present disclosure also expressly contemplates the possibility of the morcellation bag being provided with two or more different hollows.

A series of drawings are attached below in which several different embodiments of the present disclosure have been depicted in a non-limiting illustrative manner to help better understand this specification, forming an integral part thereof.

DETAILED DESCRIPTION

Throughout the present description and in the figures, elements with identical or similar functions will be denoted with the same reference numbers.

Figure 1:
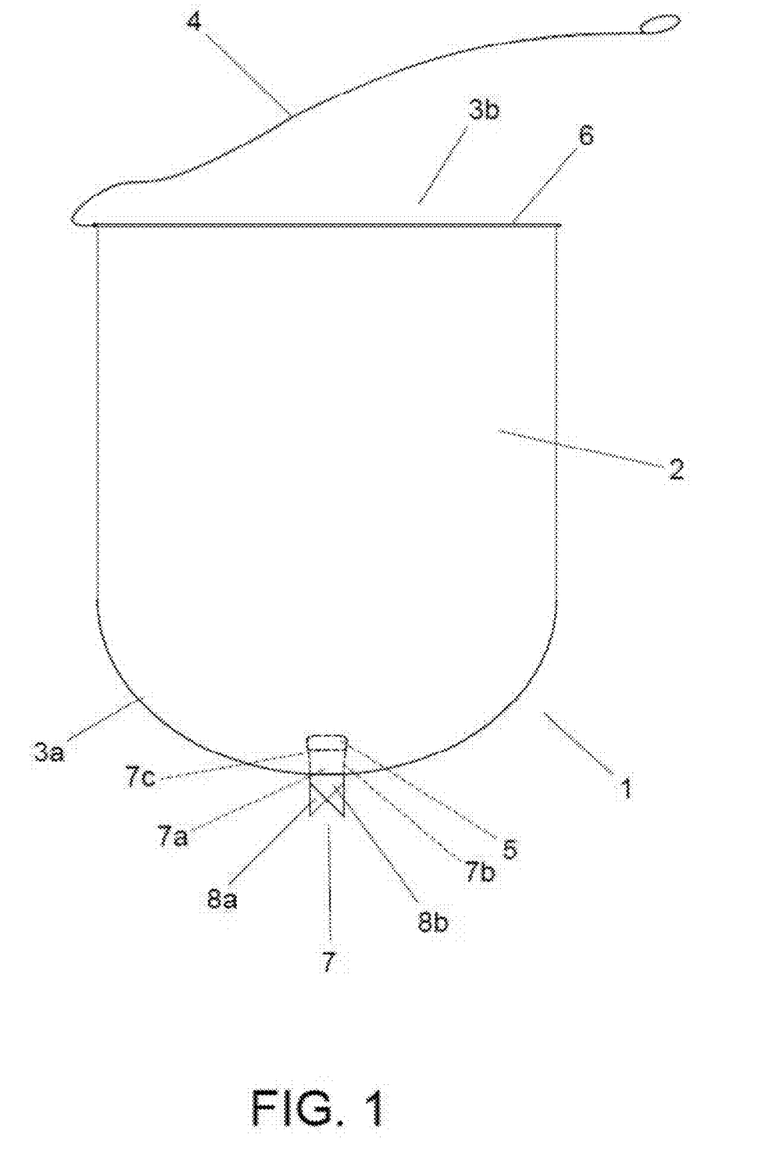
FIG. 1: is a plan view of a morcellation bag according to a first embodiment of the present disclosure.

FIG. 1 shows a first embodiment of a laparoscopic morcellation bag 1 according to the present disclosure.

In this specific embodiment of the disclosure, the bag 1 is made from a polyurethane sheet (TPU) with a thickness of 80 μm, a Shore elastic stiffness A87 (measured according to international standard DIN 53505), an elongation at break of 550% (measured according to international standard DIN EN ISO 527), a mechanical breaking strength of 60 MPa (measured according to international standard DIN EN ISO 527) and a continuous use temperature of 130° C. Said polyurethane sheet is attached along its periphery so as to define a U-shaped surface 2 of the bag, furthermore having a first closed end 3a and a second open end 3b.

In this embodiment of the disclosure, the width of the open end 3b is 18 cm.

The open end 3b is furthermore provided with a metal band-type flexible ring 6 with shape memory which facilitates the opening thereof. A single-filament drawstring 4 is also attached to the open end 3b to facilitate correct handling of the bag 1 once it has been introduced into the pelvic and/or abdominal cavity of the patient, as well as the subsequent extraction thereof from said cavity.

In this embodiment of the disclosure, there is provided at the closed end 3a a hollow 7 comprising a side surface 7b hermetically attached to the surface 2 of the closed end 3a of the bag 1. In this embodiment of the disclosure, the side surface 7b has a tubular shape and an open end, outside the bag 1, which defines the open mouth 7a and a closed bottom 7c.

In this embodiment of the disclosure, the hollow 7 has a depth of between 3 and 6 cm.

The bag 1 has at least one transparent region 5, the optical properties of this transparent region 5 being the following: total transmittance greater than 90%, clarity greater than 90% and haze less than 4%

In this specific embodiment of the disclosure, the transparent region 5 is located at the closed bottom 7c.

In other possible embodiments of the disclosure, the transparent region 5 can be:
  in addition to at the closed bottom 7c, in other parts of the surface 2 of the bag 1
  in addition to at the closed bottom 7c, on the entire surface 2 of the bag 1
  in that bag 1 that does not have a hollow 7, in at least one part of the surface 2 of the bag 1
  in that bag 1 that does not have a hollow 7, on the entire surface 2 of the bag 1

In this specific embodiment of the disclosure, the surface 2 of the bag, the side surface 7b, the closed bottom 7c and the transparent region 5 provided at said closed bottom 7c are made from one and the same polyurethane sheet (TPU). Nevertheless, the present disclosure likewise contemplates the possibility of at least two of said components: surface 2, side surface 7b, closed bottom 7c and/or transparent region 5, being made of a different material.

Likewise, two vividly colored tabs 8a, 8b, are in contact with the mouth 7a of the hollow 7. The fact that the tabs 8a, 8b are vividly colored allows them to be more readily identified during the operation of inserting the optic into the hollow.

Figure 2A:
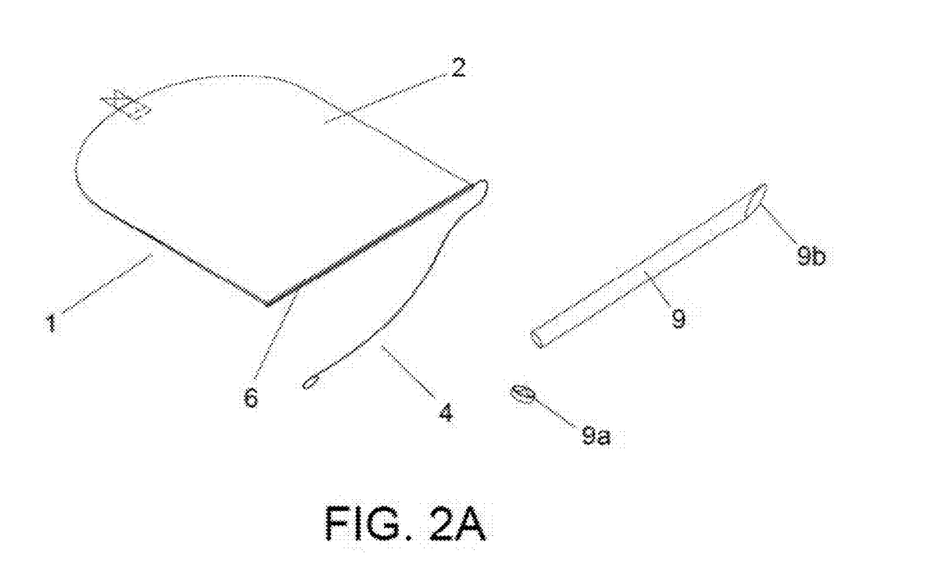
FIG. 2A: is an exploded perspective view of a first embodiment of a morcellation kit according to the present disclosure.

FIG. 2A shows a first embodiment of a morcellation kit according to the present disclosure, comprising a laparoscopic morcellation bag 1 like the one shown in FIG. 1 and an introducer tube 9.

In the embodiment shown in said FIG. 2A, the introducer tube 9 has an outer diameter of 18 mm, a length of 20 cm and is provided with a bevel 9b at one of its ends to facilitate the insertion thereof through an incision in the abdomen. The tube 9 is furthermore provided with sealing means at the opposite end, comprising a stopper 9a. Preferably, a sealing valve and a check valve are provided in the stopper 9a. Therefore, once the bag is inserted, the tube 9 can be used as a trocar for a clamp.

More preferably, the sealing valve is provided in the part of the stopper 9a which is located outside the tube 9, whereas the check valve is provided in the part of the stopper 9a which is located inside said tube 9.

Figure 2B:
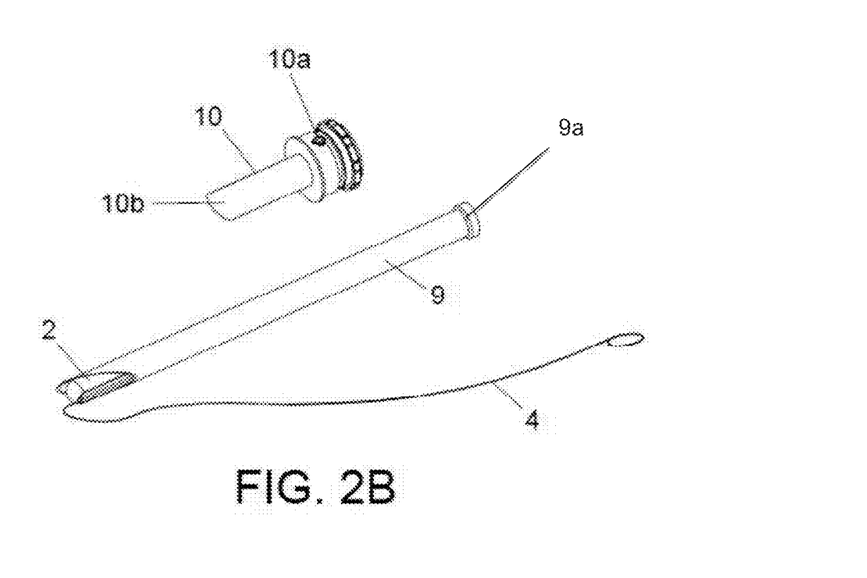
FIG. 2B: is a perspective view of the morcellation kit shown in FIG. 2a, furthermore including a trocar. This figure furthermore shows the morcellation bag folded inside the introducer tube.

FIG. 2B shows a second embodiment of a morcellation kit according to the present disclosure. In this embodiment, the surface 2 of the laparoscopic morcellation bag 1, as well as the flexible ring 6, are suitably folded and arranged inside the introducer tube 9.

The kit of FIG. 2B further comprises a trocar 10 provided with an inlet 10a for the connection of insufflation devices (not seen in the drawings). The trocar 10 further comprises a stiff sheath 10b which, in this embodiment particular of the disclosure, has an outer diameter of 20 mm and an inner diameter of 18 mm.

FIGS. 3A to 3G show, schematically and not necessarily to scale, the method of use of a morcellation kit according to the present disclosure during a laparoscopic intervention.

Figure 3A:
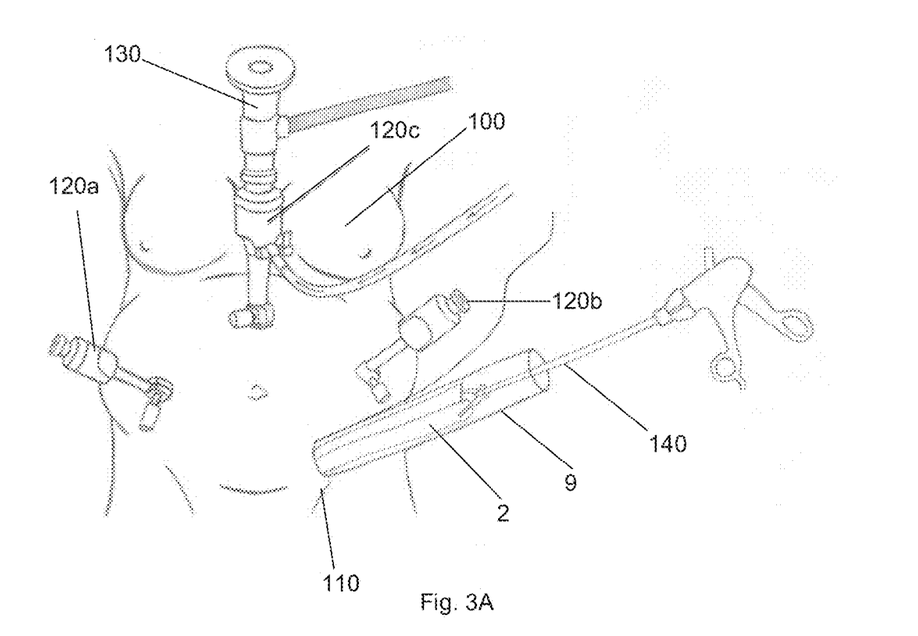
FIGS. 3A to 3G: are schematic views showing the method of use of a morcellation kit according to the present disclosure.

More particularly, FIG. 3A shows a patient 100 who will be subjected to a laparoscopic intervention. In said intervention, a first orifice 110 is made in the iliac fossa and three secondary orifices are made; there are introduced, respectively, through said secondary orifices three trocars 120a, 120b and 120c used for introducing the surgical instrument during the laparoscopic intervention and an optical device 130, which allows the medical team to maintain a view of the inside of the pelvic-abdominal cavity of the patient 100 during the intervention.

The morcellation bag 1 is introduced into the pelvic-abdominal cavity of the patient preferably through the previously made orifice 110, since this allows a better general view of the inside of said cavity (as it is the point farthest away from the optical device 130, located in the periumbilical region).

To that end, $CO_2$ is insufflated inside the pelvic-abdominal cavity of the patient through an inlet for the connection to insufflation devices (not seen in the drawings), provided in at least one of the trocars 120a, 120b or 120c. Once said cavity has been inflated, the introducer tube 9 housing the morcellation bag 1 therein folded into an accordion shape is introduced, by pushing with preferably open first clamps 140. The free end of the drawstring 4 is left outside the patient to facilitate subsequent extraction of the laparoscopic morcellation bag 1.

Figure 3B:
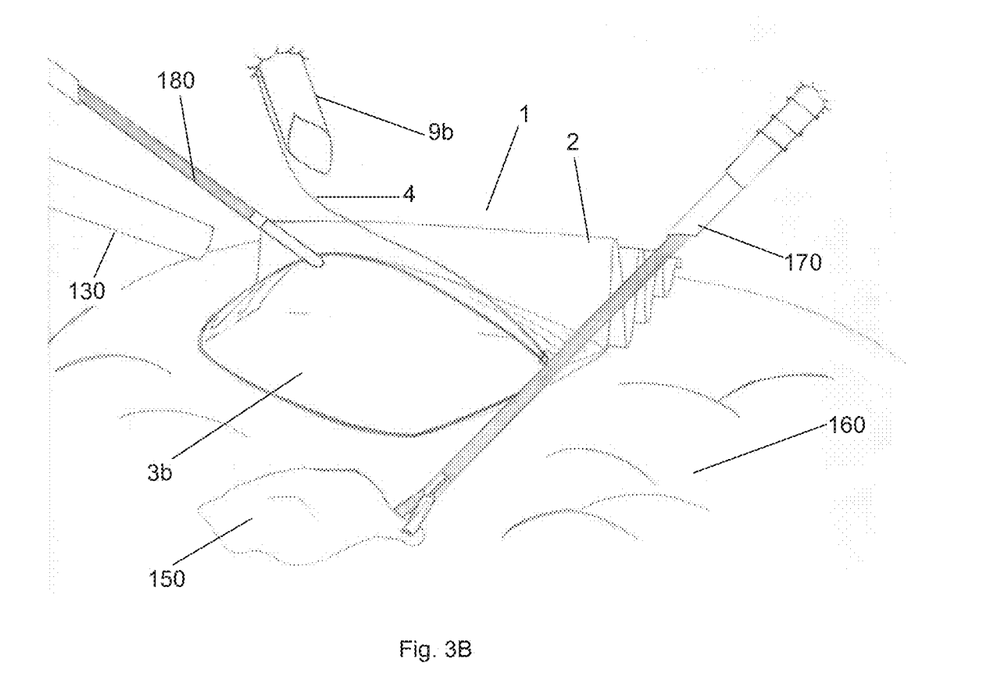

FIG. 3B schematically illustrates the process of introducing a surgical specimen 150 into the morcellation bag 1 once said bag 1 has accessed the inside 160 of the pelvic-abdominal cavity.

To perform this process, the surgical specimen 150 is handled with second clamps 170 and is introduced into the morcellation bag 1 through the open end 3b thereof, and it is kept open with the aid of third clamps 180, while the medical team observes the inside 160 of the pelvic-abdominal cavity as a result of the optical device 130.

Figure 3C:
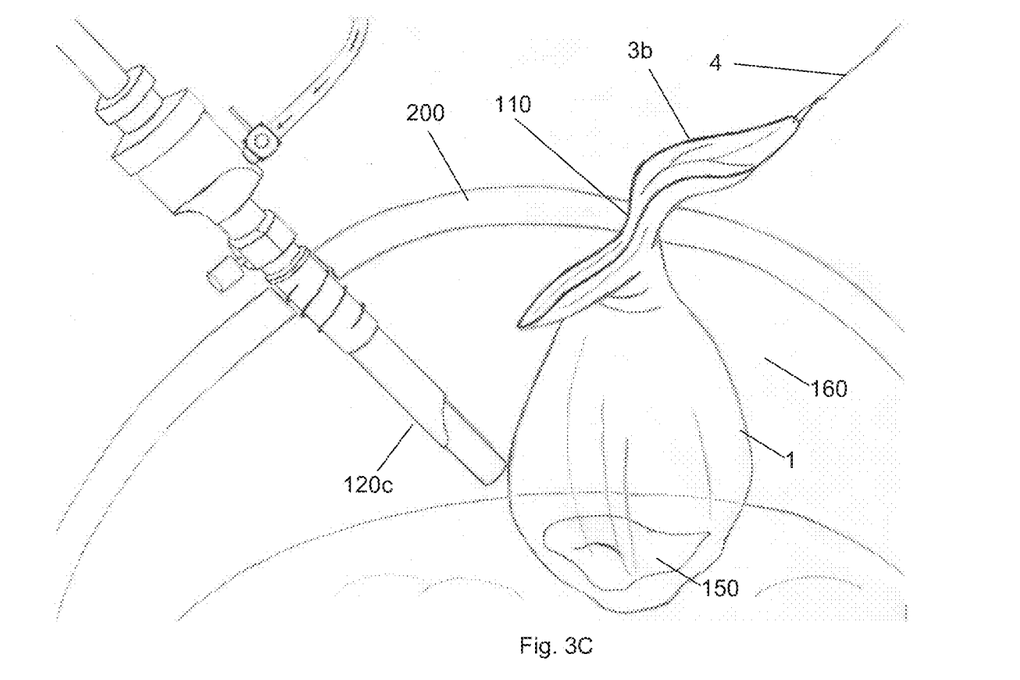

FIG. 3C schematically illustrates the manner in which, once the surgical specimen 150 has been introduced into the morcellation bag 1, the open end 3b of said bag 1 is taken out by pulling on the drawstring 4, such that it exits through the orifice 110 made in the abdominal wall 200. To facilitate the extraction of the open end 3b of the bag, can optionally be insufflated $CO_2$ through the inlet provided in the trocar 120c. Once said open end 3b has exited out, the trocar 10 is inserted through said end.

Figure 3D:
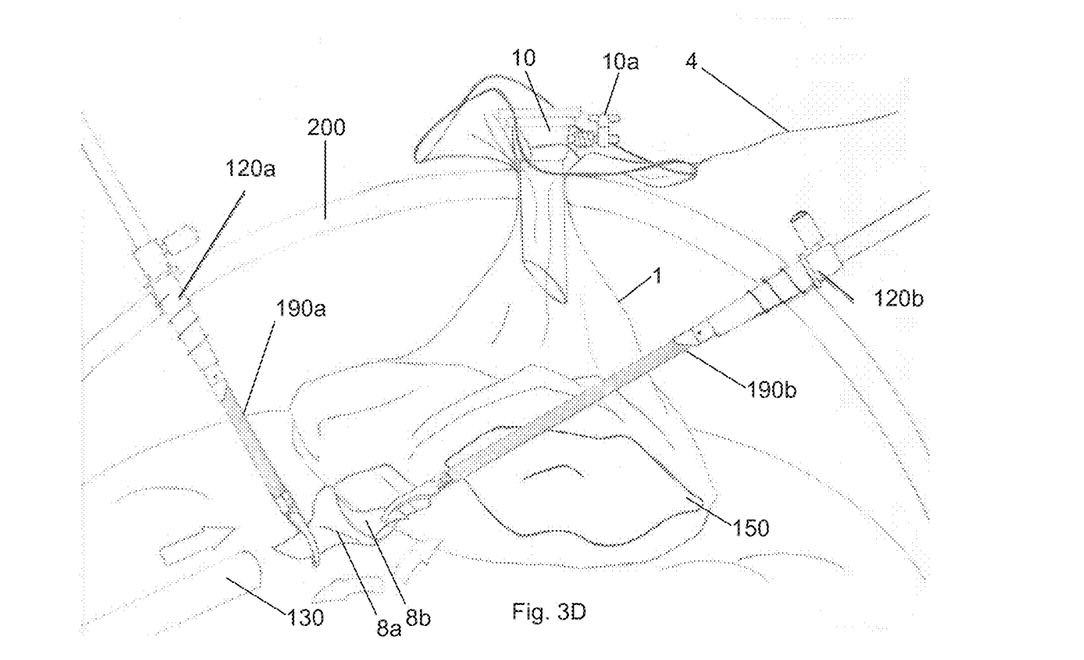

FIG. 3D schematically illustrates the manner in which the optical device 130 is placed inside the hollow 7 of the morcellation bag 1. To perform this operation, the tabs 8a and 8b are pulled by means of two additional clamps 190a and 190b while pushing the optical device 130 towards the hollow 7.

Figure 3E:
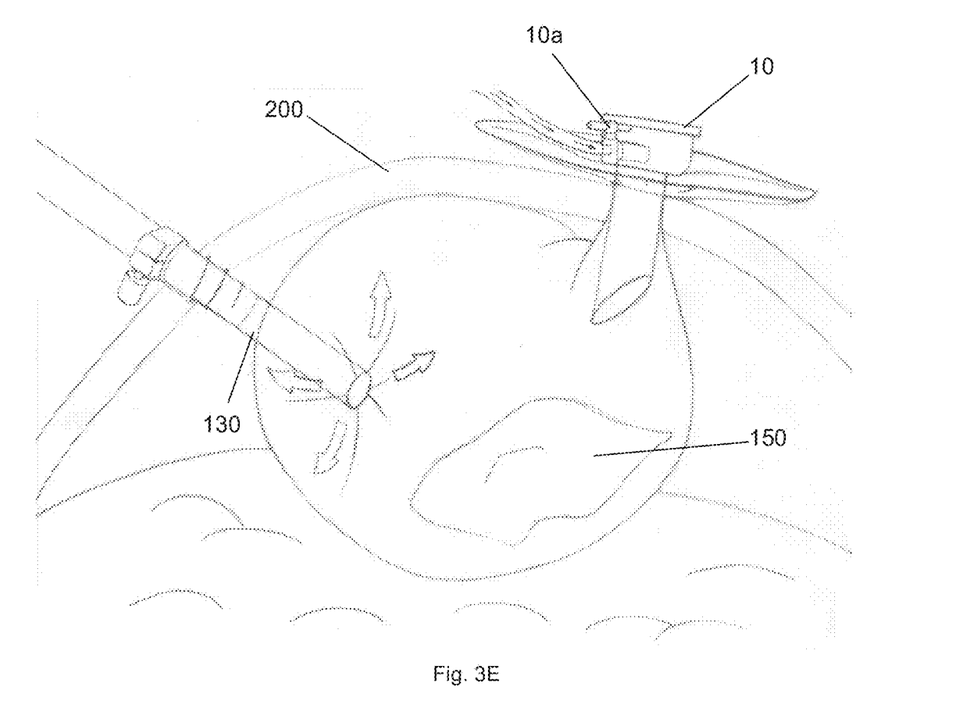

FIG. 3E depicts the optical device 130 supported at a point of the surface 2 of the bag which is located outside the hollow 7 of the morcellation bag 1. This is because in this particular case the entire surface 2 of the bag 1 is transparent, so it is not necessary to expressly place the optical device 130 in the transparent region 5 of the closed bottom 7c. To carry out this operation, the bag 1 is inflated with $CO_2$ through the trocar 10 and the abdomen of the patient is emptied, leaving the $CO_2$ to be evacuated through one of the inlets provided in the trocars 120a, 120b or 120c.

Figure 3F:
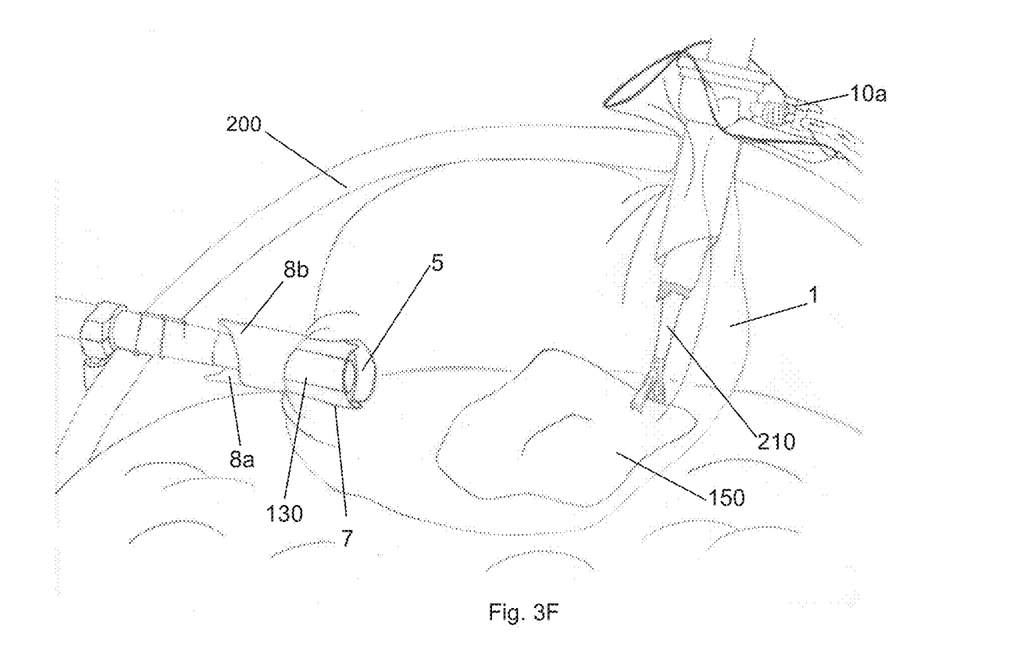

Nevertheless, as shown in FIG. 3F it would also be possible to introduce the optical device 130 into the hollow 7, contacting it with the transparent region 5 of the closed bottom 7c. In this particular case, $CO_2$ would be insufflated into the abdomen of the patient by means of the inlets provided in the trocars 120a, 120b or 120c.

FIG. 3F schematically shows the morcellation operation. In this step, the surgical specimen 150 is broken up into smaller pieces using to that end a morcellator 210 which is introduced through the trocar 10.

Figure 3G:
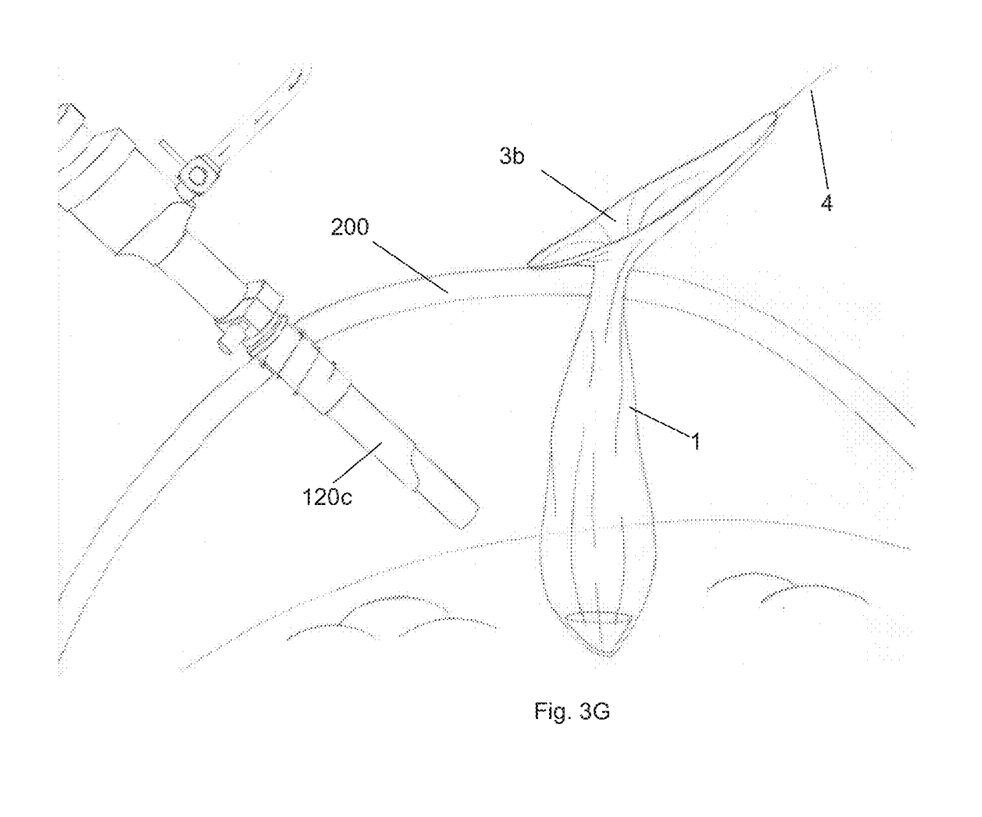

FIG. 3G shows schematically the operation of extraction final of the bag 1. In this step, the $CO_2$ is discharged from the morcellation bag 1 upon opening the valve of the trocar 10 and/or upon removing the trocar 10, and $CO_2$ is insufflated into the abdomen through the inlet of the trocar 120c so as to dilate the pelvic-abdominal cavity. This makes the bag 1 collapse. The morcellation bag 1 is subsequently removed by pulling on the outer part of said bag 1.

The invention claimed is:

1. A laparoscopic morcellation kit, comprising:
   a laparoscopic morcellation bag comprising at least one film of plastic material, attached such that it defines a surface of the bag: said surface of the bag having a first closed end and a second open end, the second open end being a port for introducing at least one surgical specimen a morcellator, the laparoscopic morcellation bag being also provided with at least one transparent region having an area of at least 1 cm² and a thickness of 80 μm;
   an introducer tube containing the laparoscopic morcellation bag folded up therein; and
   a trocar provided with an inlet for the connection to insufflation devices;
   wherein:
   the transparent region of the laparoscopic morcellation bag is made of a material or a combination of materials with a total transmittance greater than 90% measured according to international standard ASTM D 1003, a clarity greater than 90% measured according to international standard ASTM D 1003 and a haze than 4% according to international standard ASTM D 1003;
   the surface of the laparoscopic morcellation bag has a Shore elastic stiffness greater than A70 measured according to International Standard DIN 53505, an elongation at break greater than 100% measured according to International Standard DIN EN ISO 527, a mechanical breaking strength greater than 40 MPa measured according to International Standard DIN EN ISO 527 and a continuous use temperature greater than 115°C; and
   the trocar has a diameter between 15 and 20 mm and a length between 70 and 100 mm.

2. The laparoscopic morcellation kit according to claim 1, wherein the transparent region is made of polyurethane, polyester, polypropylene, polyethylene, polycarbonate, silicone and/or combinations thereof.

3. The laparoscopic morcellation kit according to any claim 1, wherein the second open end of the surface of the bag is provided with a drawstring.

4. The laparoscopic morcellation kit according to claim 3, wherein the drawstring is bent into a loop shape surrounding the second open end of the surface of the bag, said loop being part of a taut-line hitch knot type attachment.

5. The laparoscopic morcellation kit according to claim 1, wherein the second open end of the surface of the bag is provided with a flexible ring, with a Shore A hardness ≥90 and shape memory.

6. The laparoscopic morcellation kit according to claim 5, wherein the flexible ring is attached to a drawstring.

7. The laparoscopic morcellation kit according claim 1, wherein the transparent region occupies an area greater than 60% of the total area of the surface of the bag.

8. The laparoscopic morcellation kit according to claim 1, wherein the surface of the bag has a round shape.

9. The laparoscopic morcellation kit according to claim 1, wherein it is provided with at least one hollow comprising an open outer mouth, a side surface hermetically attached to the surface of the bag and a closed bottom hermetically attached to said side surface, the closed bottom furthermore being provided with a transparent region of an area of at least 1 cm² and a thickness less than 200 μm, and said transparent region being made of a material or a combination of materials with a total transmittance greater than 80%, a clarity greater than 80% and a haze less than 25%.

10. The laparoscopic morcellation kit according to claim 9, wherein the side surface of the hollow has a tubular or trapezoidal shape.

11. The laparoscopic morcellation kit according to claim 9, wherein the hollow is provided with at least one projecting tab.

12. The laparoscopic morcellation kit according to claim 1, wherein the introducer tube is provided with sealing means comprising a stopper, a sealing valve and a check valve being provided in said stopper.

* * * * *

UNITED STATES PATENT AND TRADEMARK OFFICE
CERTIFICATE OF CORRECTION

| | | |
|---|---|---|
| PATENT NO. | : 11,998,181 B2 | Page 1 of 1 |
| APPLICATION NO. | : 17/415767 | |
| DATED | : June 4, 2024 | |
| INVENTOR(S) | : Maxime Pierrick François Bureau et al. | |

It is certified that error appears in the above-identified patent and that said Letters Patent is hereby corrected as shown below:

On the Title Page

Column 1, Foreign Application Priority Data, Line 1, delete "ES201831245" and insert -- P201831245 --

In the Claims

Column 9, Line 51, Claim 1, delete "bag:" and insert -- bag; --

Column 9, Line 54, Claim 1, before "a" insert -- and --

Column 10, Line 6, Claim 1, delete "than 4%" and insert -- less than 4% measured --

Column 10, Line 17, Claim 1, delete "115°C;" and insert -- 115 °C.; --

Column 10, Line 24, Claim 3, after "to" delete "any"

Column 10, Line 33, Claim 5, delete "$\geq 90$" and insert -- $\leq 90$ --

Signed and Sealed this
Thirtieth Day of July, 2024

Katherine Kelly Vidal
*Director of the United States Patent and Trademark Office*